United States Patent [19]

Pugia et al.

[11] Patent Number: 5,716,851
[45] Date of Patent: Feb. 10, 1998

[54] GLASS/CELLULOSE AS PROTEIN REAGENT

[75] Inventors: Michael J. Pugia, Granger; Robert J. Schaeper, South Bend, both of Ind.

[73] Assignee: Bayer Corporation, Elkhart, Ind.

[21] Appl. No.: 585,719

[22] Filed: Jan. 16, 1996

[51] Int. Cl.$^6$ .................................................... G01N 21/25
[52] U.S. Cl. ............................ 436/86; 422/56; 422/61
[58] Field of Search ............................ 422/56–58, 61; 436/86

[56] References Cited

U.S. PATENT DOCUMENTS

| | | | |
|---|---|---|---|
| 5,279,790 | 1/1994 | Corey et al. | 422/56 |
| 5,424,215 | 6/1995 | Albarella et al. | 436/86 |
| 5,460,974 | 10/1995 | Kozak et al. | 436/71 |
| 5,558,834 | 9/1996 | Chu et al. | 422/57 |

*Primary Examiner*—Lyle A. Alexander
*Attorney, Agent, or Firm*—Jerome L. Jeffers

[57] ABSTRACT

Disclosed is an improvement in the method of determining protein in an aqueous fluid such as urine by contacting the fluid with a reagent system of a buffer and a protein error indicator. The improvement involves carrying out the determination in the presence of a glass/cellulose combination.

12 Claims, No Drawings

GLASS/CELLULOSE AS PROTEIN REAGENT

BACKGROUND OF THE INVENTION

The present invention is related to the detection of protein in aqueous fluids (particularly urine) by the use of a test strip containing a protein error indicator and a buffer. More particularly, it relates to the use of a particular type of material for the test strip substrate, i.e. a glass/cellulose paper.

The determination of the presence of protein in urine is important in the diagnosis of several pathological conditions affecting the kidney and circulatory systems as well as the central nervous system. It is often necessary to qualitatively and quantitatively measure protein in urine, especially in the diagnosis of diabetes and kidney disease. The predominant urine protein associated with diabetes is albumin which is the protein most commonly sought out in analysis.

Various methods for determining the presence of protein in urine are known, the most convenient of which involves wetting an absorbant test strip impregnated with a protein error indicator and buffer with a small quantity of urine. Protein error indicators are pH indicators which contain an ionizable group which is displaced in the presence of protein to provide a detectable color change. This is the same color change that the indicator would undergo under the influence of a pH change, so it is important to include buffer in the test strip to thereby avoid a pH increase since such an increase could cause the change in color in the indictor in the absence of protein thereby resulting in a false positive result. The use of protein error indicators for the determination of protein in biological samples is disclosed in U.S. Pat. No. 5,279,790 and U.S. Pat. No. 5,424,215.

Various materials have been used for the carrier material of the test strip with filter paper being the most common. While the great majority of filter papers are made from ordinary cellulosic pulp fibers, some are prepared from synthetic fibers such as glass or a mixture of pulp fibers and glass fibers. Filter papers made from glass fibers or a mixture of cellulose and glass fibers are sometimes preferred over those containing only natural cellulosic fibers because naturally occurring fibers contain peptic acids, waxy substances, electrolytes, proteins and other plant components in varying degrees. In U.S. Pat. No. 3,846,247 there is described the use of woven or matted glass fibers as the substrate in reagent strips. It has now been discovered that certain advantages are obtainable by using cellulose/glass fiber filter paper as the absorbant matrix in a test strip for the determination of protein in aqueous fluid as described above.

SUMMARY OF THE INVENTION

The present invention involves an improvement to the method of determinating protein in an aqueous fluid with a dry reagent strip comprising a solid carrier impregnated with a buffer and a protein error indicator dye wherein the interaction of the dye with the protein results in a colorimetrically detectable response. The improvement involves the use of a glass/cellulose paper as the solid carrier.

Also included within the scope of the present invention is a device for the detection of protein in an aqueous fluid which devise comprises a glass/cellulose paper as carrier which contains a protein error indicator and buffer.

DESCRIPTION OF THE INVENTION

The glass/cellulose filter papers useful in the present invention are typically prepared by the standard paper making process in which a slurry of the papermaking materials, glass and cellulosic fibers in this case, is applied to a screen and the water allowed to drain thereby leaving a residue which, when dried, possesses sufficient physical integrity for the desired purpose. Typical filter papers useful in the present invention will contain about 30 to 90 wt. % glass fibers and about 10 to 70 wt. % cellulose fibers with a concentration of from 50 to 70% glass to 50 to 30% cellulose being preferred. The cellulose portion of the glass/cellulose combination may contain cellulose groups which are derivatized such as with carboxymethyl, diethylaminoethyl, sulfoxyethyl, trimethylhydroxypropyl or mixtures thereof.

The filter paper may contain minor concentrations of extraneous material such as peptic acids, waxy substances or proteins and electrolytes. While fiber length and diameter are not critical to the practice of the present invention, fibers having a length of from 100 to 900 microns and a diameter range of from 2 to 50 microns are preferred since this range permits the physical properties of the paper such as porosity and tensile strength to be adjusted.

Protein error indicators include those pH indicators which contain an ionizable group which is displaced in the presence of a protein to provide a detectable color change. Typically, the protein error indicator is a phenolsulfonephthalein dye. Exemplary of such indicators are tetrabromophenol blue (TBBP), 5',5"-dinitro-3',3"-diiodo-3,4,5,6-tetrabromophenolsulfonephthalein (DIDNTB), coomassie brilliant blue, Fast Green FCF, Light Green SF, pyrogallol red and pyrocatechol violet.

The protein error indicators typically provide a colored response when the liquid with which they are contacted becomes more basic. Thus, DIDNTB turns from colorless to blue at a pH greater than 2.1 and TBPB turns from yellow to blue above a pH of 3.7 which color changes necessitate the presence of a buffer when the fluid being tested has a fairly high pH such as urine. This is the case because the protein error indicators contain an ionizable group which is displaced in the presence of protein to provide a detectable color change. As discussed above, it is important to include buffer in the test strip to thereby avoid a pH increase which could cause a change of color in the indicator in the absence of protein resulting in a false positive result. Suitable buffers include citric acid, phosphoric acid, citatronic acid, diglycolic acid, glycine, maleic acid, lysine, sarcosine and betaine. Tartaric acid or tartaric acid in combination with another buffer is a preferred buffer system.

The test device of the present invention is typically a strip cut from the glass/cellulose filter paper which is impregnated with the reagent system. This impregnation is typically carried out by a two dip procedure in which the first dip comprises water or a water polar organic solvent mixture in which there is dissolved the buffer (typically at a concentration of 50–750 mM) and optionally a polymer as binder and a surfactant which are included for stability and wetability as well as to prevent leaching of the buffer. The pH of this dip solution is maintained within the range of from 1.5 to 3.5 in order to keep the protein error indicator in a protenated form so that the protein is able to replace an ionizable group and form color. After drying, the strip is dipped into a second solution of an organic solvent in which is dissolved the indicator, typically in a concentration of from 0.2 to 5.0 mM, and optionally a color enhancing polymer such as Lutonal M40, a polyvinylmethylether and/or KOK 10071, a propylene glycol/carbonate copolymer.

After dipping and drying, the strips are ready for use which normally involves dipping them in a urine sample and reading the response resulting from the color change in the indicator either manually or by use of a reflectance spectrometer for better quantitation.

The method of practicing the present invention is further illustrated by the following examples:

EXAMPLE I

Filter paper segments were made into TBPB (phenolsulfonephthalein dye) reagents by cutting the segments into one inch squares and twice saturating them; first with an aqueous/ethanol mix (81.8% water/18.2% ethanol) containing a combination of 200 mM sodium citrate and 180 mM citric acid was used as buffer to maintain the mix pH at 3.7. The second saturation, after drying at 105° C. for 5 minutes, involved an ethanol mix containing the TBPB indicator dye at a concentration of 3.0 mM with drying as before.

The reagent squares were measured dry and after pipetting with water and water containing 30 mg/dL of HSA. A white square of polystyrene was used to hold the reagent samples in place on the platform of a Beckman DU-70 spectrophotometer.

The reflectance spectra of each reagent square (dye/water/HSA) were measured using a RSA BE-70 reflectance spectroscopy accessory from Labsphere, North Sutton, N.H. The background and protein response for various types of filter paper are set out in Table 1.

TABLE 1

Effect of Filter Paper on the TBPB Protein Reagent

| Paper Type | Change in Background | Change in Protein Response |
| --- | --- | --- |
| glass fiber lot A | 169% | 120% |
| glass fiber lot B | 173% | 143% |
| glass fiber lot C | 167% | 129% |
| glass fiber lot D | 165% | 146% |
| glass fiber lot E | 166% | 135% |
| glass fiber lot E refined with DI water | 118% | 123% |
| glass fiber lot F | 172% | 127% |
| quartz fiber | 109% | 126% |
| polyester lot A | 105% | 130% |
| polyester lot B | 113% | 72% |
| porous firm polyethylene | 162% | 81% |
| bulky wood pulp | 188% | 90% |
| bleached softwood pulp | 94% | 121% |
| bleached softwood pulp refined with DI water | 122% | 69% |
| bleached softwood pulp with second refining | 108% | 83% |
| bleached eucalyptus wood pulp | 58% | 144% |
| cotton linter lot A, fiber length of 1200–2500 | 121% | 92% |
| cotton linter lot B, fiber length of 1200–2500 | 99% | 115% |
| cotton linter lot C, fiber length of 1200–2500 | 146% | 118% |
| cotton linter lot D, fiber length of 1200–2500 | 196% | 63% |
| cotton linter lot D refined with DI water | 118% | 97% |
| cotton linter lot D with second refining | 101% | 118% |
| cotton linter with fiber length of 700–1000 | 139% | 71% |
| cotton linter with fiber length of 3600–4240 | 152% | 56% |
| cotton linter with fiber length of 4900–5800 | 157% | 51% |
| cotton linter with fiber length of min. 7900 | 174% | 52% |
| cotton linter with fiber length of 2500–3300 | 165% | 44% |
| cotton linter lot A, fiber length of 1200–1600 | 160% | 35% |
| cotton linter lot B, fiber length of 1200–1600 | 146% | 55% |
| cotton/wood Standard | 100% | 100% |
| cotton/wood standard lot B | 104% | 113% |
| cotton/wood Lot B, refined with DI water | 107% | 111% |
| cotton/silica gel | 160% | 14% |
| 30% cotton linter / 70% glass | 110% | 251% |

In Table 1, the background is based on the result with plain water and the protein response is based on the difference observed with water/protein and in water. Ideally, a reagent will exhibit a lower or equal background and larger protein response than the control. This is the case because the lower the background the more specific the test, i.e. less high specific gravity urine interference, and the larger the protein response the greater the sensitivity to protein. Microalbuminuria is an example of the need to measure low protein levels accurately. In this experiment a cotton/wood standard filter paper exhibiting changes in background and protein response of 100% each was chosen as control. These 100% changes were background and protein response obtained with a standard filter paper having been assigned a value of 100%. The background and protein response obtained with each paper type is reported relative to the standard. For example, a background of 146% is 46% greater than the background of the standard. An increased protein response is particularly important when measuring microalbuminuria, in which the protein is normally present in urine in concentrations of 3–8 mg/dL as well as in the case with proteinuria in which the protein is normally present in concentrations of 15–30 mg/dL.

From Table 1 it can be determined that filter paper F255-03 from Whatman Ltd., which is a cotton glass paper comprising 30% cotton linter (which typically have fiber lengths from 500 to 3000 microns) and 70% glass did the best job of accomplishing the dual goals of maintaining a constant background (110% of control) and exhibiting an increase in protein response (251% of control). In contrast, the glass fiber lot B, while exhibiting a change in protein response of 143% also exhibited an increase in background which is unacceptable because it can result in high SG urines being read as false positives. On the other end of this spectrum is bleached softwood wood pulp based filter paper which, while providing a slight reduction in background, demonstrated an increase in protein response of only 21% as compared to the control reagent.

The fiber length for the glass and cellulose in the filter paper is not important for protein response. Microcrystalline cellulose, which typically has a fiber length of from 25 to 100 microns, could be used as well. Fiber length does, however, affect physical properties of the paper such as porosity and tensile strength.

EXAMPLE II

Filter paper strips were made into protein reagent strips and tested as in Example I except that another phenolsulfonephthalein dye, 5',5"-dinitro-3',3"-diiodo-3,4,5,6-tetrabromophenolsulfonephthalein (DIDNTB); was used.

In this experiment, filter papers were made into dry DIDNTB protein reagents and processed into reagent strips which were tested on a Clinitek-200+ instrument from Bayer Diagnostics after dipping them into urine containing 0 or 8 mg/dL of human serum albumin (HSA). Prior to addition of the HSA, the urine was filtered through a filtration membrane to remove all naturally occurring protein.

The DIDNTB protein reagent was made from two saturations of filter paper, the first of which was an aqueous/ethanol mix containing a buffer (sodium citrate) a polymer enhancer and, in some cases binding polymer and polyvinyl alcohol to increase the wet tensile strength of the paper. The mix pH was adjusted to 2.1 using sodium hydroxide and hydrochloric acid. The second saturation was a toluene/THF mix containing DIDNTB and enhancer polymers, i.e. Lutanol M40 and KOK 10071. The mix solutions; whose elements are identified as to function, preferred concentration and allowable range; are set out in Table 2; were used to saturate the filter paper and the paper was dried at 105° C. for 7 minutes after each saturation.

TABLE 2

DIDNTB Protein Reagent Composition

| Ingredient | Prefer Conc. Function | used | Allowable Range |
|---|---|---|---|
| 1st application | | | |
| water | Solvent | 1000 mL | — |
| Ethanol | Solvent | 8.15 mL | 0–40 g% |
| PVA polymer | Binder | 0.25 g% | 0–5 g% |
| Sodium citrate | Buffer | 8.68 (378 mM) | 50–750 mM |
| pH | — | 2.1 | 1.5–3.5 |
| 2nd application | | | |
| Toluene | Solvent | 95 mL | — |
| THF | Solvent | 5 mL | 0–50 mL |
| DIDNTB | Indicator | 0.329 g (3 mM) | 0.2–5.0 mM |
| Lutonol M40 | Polymer enhancer | 0.143 g% | 0–1.0 g% |
| KOK 10071 | Polymer enhancer | 0.375 g% | 0–10.0 g% |

DIDNTB = 5',5''-Dinitro-3',3''-Diiodo-3,4,5,6-Tetrabromophenolsulfonephthalein

The results of this experiment, which was carried out using several different types of cellulose/glass filter paper as well as one all glass matrix and several straight cellulose filter papers are set out in Table 3.

TABLE 3

Effect of Filter Paper on the DIDNTB Protein Reagent.

| Matrix | % Glass | Absorp mg/cm$^2$ | Thick μm | Protein Response (Δ%R @ 610 nm) 0 to 8 mg/dL |
|---|---|---|---|---|
| glass | 100 | 16 | 690 | 0.5 |
| cellulose | 0 | 10 | 363 | 12.1 |
| cellulose | 0 | 16 | 710 | 6.8 |
| cellulose | 0 | 19 | 710 | 6.8 |
| cellulose | 0 | 19 | 840 | 12.0 |
| cellulose | 0 | 21 | 685 | 12.5 |
| cellulose | 0 | 20 | 620 | 14.0 |
| cellulose | 0 | 22 | 890 | 11.5 |
| cellulose | 0 | 22 | 741 | 15.6 |
| cell:glass | 70 | 13 | 371 | 27.1 |
| cell:glass | 90 | 21 | 552 | 31.1 |
| cell:glass | 70 | 12 | 266 | 23.1 |
| diethylaminoethyl cell:glass | 70 | 11 | 335 | 21.4 |
| trimethylhydroxy propyl cell:glass | 70 | 20 | 373 | 21.4 |
| carboxymethyl cell:glass | 70 | 16 | 402 | 29.0 |
| sulfoxyethyl cell:glass | 70 | 11 | 392 | 28.9 |
| orthophosphate cell:glass | 70 | 13 | 313 | 12.2 |
| carboxymethyl cell:glass:glass:PVA | 70 | 15 | 458 | 23.0 |
| trimethylhydroxy propyl cell:glassPVA | 70 | 18 | 453 | 33.0 |
| cellulose:glass:PVA | 90 | 12 | 273 | 28.7 |
| cellulose:glass:PVA | 50 | 13 | 273 | 20.0 | cell = microcrystalline cellulose

From Table 3 it can be determined that the improvement in protein response is observed with a dye other than TBBP. The sole exception, i.e. orthophosphate cellulose:glass, probably failed to improve protein response because of prevention of protein interaction with the dye. The addition of PVA to the cellulose/glass formulations did not alter the results.

While the present invention is not predicated upon any particular theory or method of operation, it is believed that the improved response observed with glass/cellulose may be attributable to decreased interactions between the matrix and the reagent chemicals/sample protein.

What is claimed is:

1. In the method of determining protein in an aqueous fluid which comprises contacting the aqueous fluid with a reagent comprising a buffer and a protein error indicator dye wherein the reaction of the dye with the protein results in a colorimetrically detectable response from the dye, the improvement which comprises carrying out the method in the presence of a glass/cellulose combination wherein the glass is present in an amount of from 30 to 90 weight percent of the glass/cellulose combination and the cellulose is present in an amount of from 10 to 70 weight percent of the glass/cellulose combination.

2. The method of claim 1 wherein the glass/cellulose combination is a paper comprised of glass and cellulose fibers which is used as a support for the reagents.

3. The method of claim 1 wherein the glass/cellulose paper contains from 50 to 70% glass:50 to 30% cellulose.

4. The method of claim 1 wherein the cellulose portion of the combination contains derivatized cellulose groups.

5. The method of claim 3 wherein the derivatized cellulose groups are carboxymethyl, diethylaminoethyl, sulfoxyethyl, trimethylhydroxypropyl, or a mixture thereof.

6. The method of claim 1 wherein the protein error indicator is a phenolsulfonephthalein dye.

7. The method of claim 6 wherein the phenolsulfonephthalein dye is tetrabomophenol blue 5',5"-dinitro-3',3"-diiodo-3,4,5,6-tetrabomophenosulfonephthalein, coomassie brilliant blue, Fast Green FCF, Light Green SF, pyrogallol red or pyrocatechol violet.

8. The method of claim 1 wherein the aqueous fluid is urine.

9. A device for the determination of protein in an aqueous fluid which comprises a glass/cellulose paper as substrate in which there is absorbed a buffer and a protein error indicator dye which dye exhibits a colorimetrically detectable response upon being contacted with an aqueous fluid containing protein wherein the glass is present in an amount of from 30 to 90 weight percent of the glass/cellulose paper and the cellulose is present in an amount of 10 to 70 weight percent of the glass/cellulose paper.

10. The device of claim 9 wherein the glass/cellulose paper contains from 50 to 70% glass:50 to 30% cellulose.

11. The device of claim 9 wherein the protein error indicator is a phenolsulfonephthalein dye.

12. The device of claim 11 wherein the phenosulfonephthalein dye is tetrabromophenol blue, 5',5"-dinitro-3',3"-diiodo-3,4,5,6-tetrabromophenosulfonephthalein, coomassie brilliant blue, Fast Green FCF, Light Green SF, pyrogallol red or pyrocatechol violet.

* * * * *